United States Patent
Reckelhoff et al.

(10) Patent No.: US 9,801,791 B2
(45) Date of Patent: Oct. 31, 2017

(54) MEDICATION DISPENSING CART

(71) Applicant: MV Circuit Design, Inc., Vermillion, OH (US)

(72) Inventors: Ray Reckelhoff, Elgin, SC (US);
Markos P. Paradissis, Vermillion, OH (US); William Colley, III, Oberlin, OH (US); Neil Kammiller, Lorain, OH (US); Michael Mott, Elyria, OH (US)

(73) Assignee: MV Circuit Design Inc., Vermillion, OH (US)

( * ) Notice: Subject to any disclaimer, the term of this patent is extended or adjusted under 35 U.S.C. 154(b) by 0 days.

(21) Appl. No.: 14/327,275

(22) Filed: Jul. 9, 2014

(65) Prior Publication Data

US 2015/0100154 A1    Apr. 9, 2015

Related U.S. Application Data

(63) Continuation of application No. 13/461,615, filed on May 1, 2012, now Pat. No. 8,812,153, which is a
(Continued)

(51) Int. Cl.
*A61J 7/00* (2006.01)
*G06F 19/00* (2011.01)
(Continued)

(52) U.S. Cl.
CPC .......... *A61J 7/0084* (2013.01); *A61G 12/001* (2013.01); *G06F 17/00* (2013.01);
(Continued)

(58) Field of Classification Search
CPC . A61J 7/0084; A61G 12/001; A61G 2203/44; G06F 19/3462; G06F 17/00; G07F 17/0092
(Continued)

(56) References Cited

U.S. PATENT DOCUMENTS 4,202,586 A    5/1980 Oplinger
4,368,867 A    1/1983 Pendleton et al.
(Continued)

FOREIGN PATENT DOCUMENTS

CH    688607 A5    12/1997
DE    8114991 U    10/1981
(Continued)

OTHER PUBLICATIONS

Advertisement for Ergotron Mobile Work Centers, Integrated Design and Manufacturing, Feb. 1997. 1 page.
(Continued)

*Primary Examiner* — Michael K Collins
(74) *Attorney, Agent, or Firm* — Renner, Otto, Boisselle & Sklar, LLP

(57) ABSTRACT

A medication dispensing cart having a computer and monitor, a work surface with pull out keyboard, and plural drawers arranged as a vertical series of cassettes that can be added as needed. The battery powered device uses software and pass codes for controlling access to each drawer, and requires a second pass code for any drawer designated to contain narcotics. Records can be kept of who dispenses what medication and when for each cart in a system of carts. The cart in the system is in wireless communication with a system administrator. Emails alerting the system administrator of low battery power, of a cart switching to off, of an attempted break-in, and of inventory and usage data are sent automatically by email.

11 Claims, 7 Drawing Sheets

Related U.S. Application Data continuation of application No. 12/278,263, filed as application No. PCT/US2007/003765 on Feb. 12, 2007, now Pat. No. 8,180,485.

(60) Provisional application No. 60/772,416, filed on Feb. 11, 2006.

(51) Int. Cl.
 *A61G 12/00* (2006.01)
 *G07F 17/00* (2006.01)
 *G06F 17/00* (2006.01)

(52) U.S. Cl.
 CPC ...... *G06F 19/3462* (2013.01); *G07F 17/0092* (2013.01); *A61G 2203/44* (2013.01)

(58) Field of Classification Search
 USPC .................................................. 700/242, 243
 See application file for complete search history.

(56) References Cited

U.S. PATENT DOCUMENTS

| | | |
|---|---|---|
| 4,372,515 A | 2/1983 | Noonan |
| 4,471,931 A | 9/1984 | Covey et al. |
| D279,007 S | 5/1985 | Empson et al. |
| 4,556,189 A | 12/1985 | Kirpluk et al. |
| 4,561,620 A | 12/1985 | Goetz et al. |
| 4,575,033 A | 3/1986 | Henneberg et al. |
| 4,589,621 A | 5/1986 | Hunt et al. |
| 4,616,218 A | 10/1986 | Bailey et al. |
| 4,640,199 A | 2/1987 | Zigman |
| 4,645,153 A | 2/1987 | Granzow et al. |
| D289,873 S | 5/1987 | Gemmell et al. |
| 4,681,378 A | 7/1987 | Hellman |
| D293,382 S | 12/1987 | Ichikawa |
| 4,717,112 A | 1/1988 | Pirkle |
| 4,726,633 A | 2/1988 | Noble et al. |
| 4,729,533 A | 3/1988 | Hillary et al. |
| D295,415 S | 4/1988 | Thies et al. |
| 4,769,634 A | 9/1988 | Killian, Jr. et al. |
| 4,834,329 A | 5/1989 | Delapp |
| 4,836,478 A | 6/1989 | Sweere |
| 4,836,486 A | 6/1989 | Vossoughi et al. |
| 4,851,756 A * | 7/1989 | Schaller ............... H02J 7/0024 307/46 |
| 4,852,500 A | 8/1989 | Ryburg et al. |
| 4,918,841 A | 4/1990 | Turner et al. |
| 4,919,387 A | 4/1990 | Sampson |
| D310,358 S | 9/1990 | Nuttall et al. |
| 4,967,928 A | 11/1990 | Carter |
| D312,630 S | 12/1990 | Esslinger |
| 4,989,291 A | 2/1991 | Parent |
| D317,912 S | 7/1991 | Takai |
| D319,405 S | 8/1991 | Brawne |
| D319,435 S | 8/1991 | Brown |
| 5,039,928 A | 8/1991 | Nishi et al. |
| 5,041,770 A | 8/1991 | Seiler et al. |
| D326,847 S | 6/1992 | Savio |
| 5,149,030 A * | 9/1992 | Cockrill ................ A61G 1/04 248/129 |
| 5,174,223 A | 12/1992 | Nagy et al. |
| 5,217,064 A | 6/1993 | Kellow et al. |
| D337,104 S | 7/1993 | Orchard |
| D339,796 S | 9/1993 | Goodner et al. |
| 5,260,885 A | 11/1993 | Ma |
| 5,277,392 A | 1/1994 | Rossman et al. |
| 5,287,815 A | 2/1994 | Gross |
| D344,933 S | 3/1994 | Wiseman et al. |
| 5,321,579 A | 6/1994 | Brown et al. |
| D348,449 S | 7/1994 | Rodd et al. |
| D349,489 S | 8/1994 | Wang |
| 5,362,025 A | 11/1994 | Trom et al. |
| D354,052 S | 1/1995 | Imai |
| D354,952 S | 1/1995 | Rodd |
| D357,468 S | 4/1995 | Rodd |
| 5,437,235 A | 8/1995 | Randolph |
| 5,442,512 A | 8/1995 | Bradbury |
| 5,473,997 A | 12/1995 | Solomon et al. |
| 5,486,058 A | 1/1996 | Chan |
| 5,522,323 A | 6/1996 | Richard |
| 5,536,084 A | 7/1996 | Curtis et al. |
| D377,720 S | 2/1997 | Miller et al. |
| 5,630,566 A | 5/1997 | Case |
| 5,687,717 A | 11/1997 | Halpern et al. |
| 5,694,199 A | 12/1997 | Rodriguez |
| D393,382 S | 4/1998 | Rutter et al. |
| 5,738,316 A | 4/1998 | Sweere et al. |
| 5,772,637 A | 6/1998 | Heinzmann et al. |
| 5,775,234 A | 7/1998 | Solomon et al. |
| 5,806,943 A | 9/1998 | Dell et al. |
| 5,822,185 A | 10/1998 | Cavello |
| 5,842,672 A | 12/1998 | Sweere et al. |
| 5,868,079 A | 2/1999 | Charny |
| 5,897,179 A | 4/1999 | Wade |
| 5,918,841 A | 7/1999 | Sweere et al. |
| 5,960,901 A | 10/1999 | Hanagan |
| 5,971,341 A | 10/1999 | Pfister |
| 5,992,953 A | 11/1999 | Rabinovitz |
| 6,022,088 A | 2/2000 | Metzler |
| 6,029,580 A | 2/2000 | Alfonso et al. |
| 6,061,104 A | 5/2000 | Evanicky et al. |
| 6,085,972 A | 7/2000 | Wright |
| 6,098,936 A | 8/2000 | Birrell |
| 6,170,929 B1 | 1/2001 | Wilson et al. |
| 6,175,779 B1 | 1/2001 | Barrett |
| 6,199,952 B1 | 3/2001 | Davis |
| 6,269,753 B1 | 8/2001 | Roddan |
| 6,298,794 B1 | 10/2001 | Brown |
| 6,339,732 B1 | 1/2002 | Phoon et al. |
| 6,389,992 B1 | 5/2002 | Miller |
| 6,394,402 B2 | 5/2002 | Coonan et al. |
| 6,431,580 B1 | 8/2002 | Kady |
| 6,435,109 B1 | 8/2002 | Dell et al. |
| 6,493,220 B1 * | 12/2002 | Clark ...................... A47B 21/00 248/918 |
| 6,557,955 B2 | 5/2003 | Saravis |
| 6,604,019 B2 | 8/2003 | Ahlin et al. |
| 6,626,445 B2 | 9/2003 | Murphy et al. |
| 6,721,178 B1 * | 4/2004 | Clark et al. ................. 361/679.4 |
| 6,775,591 B1 | 8/2004 | Shoenfeld |
| 6,816,145 B1 | 11/2004 | Evanicky |
| 6,996,455 B2 | 2/2006 | Eggenberger et al. |
| 7,009,840 B2 * | 3/2006 | Clark et al. ................. 361/679.41 |
| 7,134,673 B2 | 11/2006 | Ferraro et al. |
| 7,142,944 B2 | 11/2006 | Holmes et al. |
| 7,154,397 B2 | 12/2006 | Zerhusen et al. |
| 7,594,668 B2 | 9/2009 | Arceta et al. |
| 7,630,791 B2 | 12/2009 | Nguyen et al. |
| 7,747,347 B2 | 6/2010 | Park, IV |
| 8,180,485 B2 * | 5/2012 | Reckelhoff .................... 700/242 |
| 8,196,939 B2 | 6/2012 | Bustle et al. |
| 8,412,375 B2 | 4/2013 | Schifman et al. |
| 8,812,153 B2 * | 8/2014 | Reckelhoff .................... 700/243 |
| 9,192,772 B1 * | 11/2015 | Tsukamoto .......... A61N 1/3787 |
| 2001/0002448 A1 | 5/2001 | Wilson et al. |
| 2001/0032035 A1 | 10/2001 | Holmes et al. |
| 2002/0000092 A1 | 1/2002 | Sharood et al. |
| 2002/0074905 A1 | 6/2002 | Tiramani et al. |
| 2002/0171332 A1 | 11/2002 | Skov et al. |
| 2003/0159076 A1 | 8/2003 | Delisle et al. |
| 2005/0140510 A1 | 6/2005 | Elwood et al. |
| 2005/0178298 A1 * | 8/2005 | Rossini .............. A47B 21/0314 108/50.01 |
| 2005/0201345 A1 * | 9/2005 | Williamson ........ G06F 19/3456 370/338 |
| 2005/0279122 A1 | 12/2005 | Cohen et al. |
| 2005/0288571 A1 * | 12/2005 | Perkins ............... A61B 5/0002 600/407 |
| 2006/0005876 A1 | 1/2006 | Gaudiana et al. |
| 2006/0125356 A1 * | 6/2006 | Meek, Jr. ............. A61G 12/001 312/215 |
| 2007/0069491 A1 | 3/2007 | Ferraro et al. |

(56) References Cited

U.S. PATENT DOCUMENTS

| | | | |
|---|---|---|---|
| 2007/0078562 A1* | 4/2007 | Park, IV | A61G 12/001 700/243 |
| 2007/0228680 A1 | 10/2007 | Reppert et al. | |
| 2007/0299358 A1* | 12/2007 | Bertinetti | A61G 12/001 600/529 |
| 2009/0132090 A1 | 5/2009 | Kaczmarz et al. | |
| 2009/0159608 A1 | 6/2009 | Shoenfeld | |
| 2009/0231132 A1 | 9/2009 | Shoenfeld | |
| 2009/0312656 A1 | 12/2009 | Lau et al. | |
| 2010/0004780 A1 | 1/2010 | Rickelhoff | |
| 2010/0042437 A1 | 2/2010 | Levy et al. | |
| 2010/0102280 A1 | 4/2010 | Ford et al. | |
| 2010/0106291 A1 | 4/2010 | Campbell et al. | |
| 2010/0218021 A1 | 8/2010 | Ma et al. | |
| 2010/0222649 A1 | 9/2010 | Schoenberg | |
| 2010/0241446 A1 | 9/2010 | Eckert et al. | |
| 2010/0275625 A1 | 11/2010 | Lowenstein | |
| 2010/0300130 A1 | 12/2010 | Shoenfeld et al. | |
| 2012/0176245 A1 | 7/2012 | Paydar et al. | |
| 2012/0203377 A1 | 8/2012 | Paydar et al. | |

FOREIGN PATENT DOCUMENTS

| | | |
|---|---|---|
| DE | 295 06 433 U1 | 8/1995 |
| DE | 196 42 425 A1 | 4/1996 |
| DE | 195 36 664 A1 | 4/1997 |
| DE | 196 50 100 A1 | 6/1998 |
| EP | 0 145 410 A2 | 6/1985 |
| EP | 0 321 137 A2 | 6/1989 |
| EP | 0 796 575 A1 | 9/1997 |
| FI | 974408 A | 6/1999 |
| JP | 5161510 A | 6/1993 |
| JP | 913939 | 1/1997 |
| JP | 9262137 A | 10/1997 |
| JP | 10-011172 | 1/1998 |
| JP | 10-057157 A | 3/1998 |
| JP | 10-146224 A | 6/1998 |
| JP | 11-127976 A | 5/1999 |
| WO | 97/46824 A1 | 12/1997 |

OTHER PUBLICATIONS

Author Unknown, "24" Wide AnthroCart," Anthro Technology Furniture, Date Unknown. [retrived on Mar. 19, 2007]. 4 pages. Retrieved from: http://web.archive.org/web/19970521181347/www.anthro.com/hprods_a/p_3.html.
Author Unknown, "All the Right Moves . . . ," Flat Panel Monitor Mounting Solutions. Ergotron, Inc., 1997, 4 pages.
Author Unknown, "CMS Business," Fieldlink, Ergotron Nov. 1997, 3 pages.
Author Unknown, "Computer/Storage Cart," Milcare, Inc., 1997, 2 pages.
Author Unknown, "Ergotron ErgoCart," Product Bulletin, Ergotron, Inc., Dec. 1997, 2 pages.
Author Unknown, "Ergotron ErgoLift," Product Bulletin, Ergotron, Inc., Apr. 1999, 3 pages.
Author Unknown, "Evaluation Program: Mobile WorkCentor Solutions," Ergotron, Inc., 1997, 5 pages.
Author Unknown, "Flat Panel Monitor, Keyboard & Laptop," ARMS Product Guide, Ergotron, Inc., 1997, 8 pages.
Author Unknown, "Ira Goldklang's TRS-80 Revived Site: Model 200 Page," Aug. 5, 2007, [retrieved on Mar. 24, 2008], 3 pages. Retrieved from: http://www.trs-80.com/trs80-models-model200.htm.
Author Unknown, "Korean Makers of TFT-LCD Likely to Have Brisk Year," AsiaPulse News, Jan. 11, 1999, 1 page.
Author Unknown, "MediComp 2001 Options and Accessories," Jaco, Inc., 1997, 1 page.
Author Unknown, "MLT 2001: Variable Height Laptop/Peripheral Cart," Jaco Inc., 1997, 3 pages.
Author Unknown, "Mobile WorkCenter System," Ergotron, Inc., 1997, 5 pages.
Author Unknown, "Mobile WorkCenters: Featuring Ergotron's Patented Monitor Suspension System," Ergotron, Inc., 1994, 4 pages.
Author Unknown, "PCT-SC: Ergonomically designed Trans-Mobile self-contained clinical computing workstation system," Tremont Medical, 1997, 2 pages.
Author Unknown, "Point-of-Care Carts as part of a Clinical Information System," MMP MedCart, date unknown, 8 pages.
Author Unknown, "Point-of-Care: Cart Systems," MMP MedCart, 1997, 2 pages, Retrieved from: http://web.archive.org/web/19970301233615/www.medcart.com/pointof.html.
Author Unknown, "Technology Furniture," Anthro, Date Unknown, 40 pages.
Author Unknown, "Technology Furniture: New Product Update Fall 1996," Anthro, 1996, 12 pages.
Author Unknown, "The Ergotron ErgoCart: A mobile and height adjustable solution for an entire computer system," Product Sheet, Ergotron, Inc., May 1999, 2 pages.
Author Unknown, "The Ergotron ErgoCart: A Mobile Solution for an entire computer system," Product Sheet, Ergotron, Inc., Apr. 1998, 2 pages.
Author Unknown, "The Nursing Station on Wheels," Infoport, Sculptor Development Technologies, Inc., Date Unknown, [retrieved on Mar. 24, 2008], 2 pages. Retrieved from: http://www.sculptorsoftware.com/infoport.asp.
Author Unknown, "Welcome to Ergotron," Ergotron, Inc., 1996, [retrieved on Sep. 17, 2009], 1 page. Retrieved from: http://web.archive.org/web/19961104052222/http://www.ergotron.com/.
Bassak, G., "Sharp picture, Fuzzy Forecasting," Business & Company Resource Center, Electronic Buyers' News, Jan. 31, 2000, 3 pages.
International Search Report and Written Opinion of PCT/US07/76336 dated Aug. 13, 2008, 6 pages.
International Search Report and Written Opinion of PCT/US11/63505, dated Apr. 26, 2012, 9 pages.
International Search Report and Written Opinion of PCT/US11/63597, dated Apr. 13, 2012, 14 pages.
International Search Report and Written Opinion of PCT/US07/03765 dated Jun. 3, 2008, 4 pages.

* cited by examiner

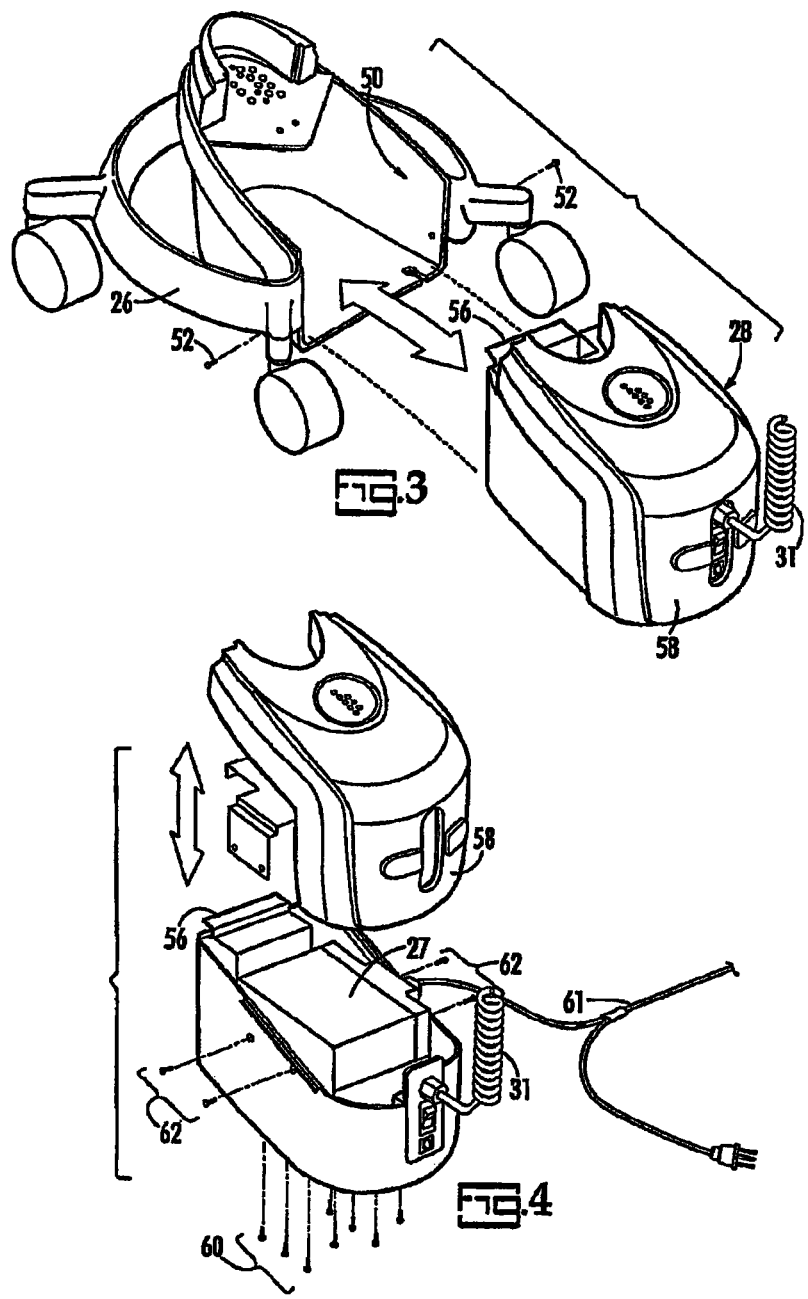

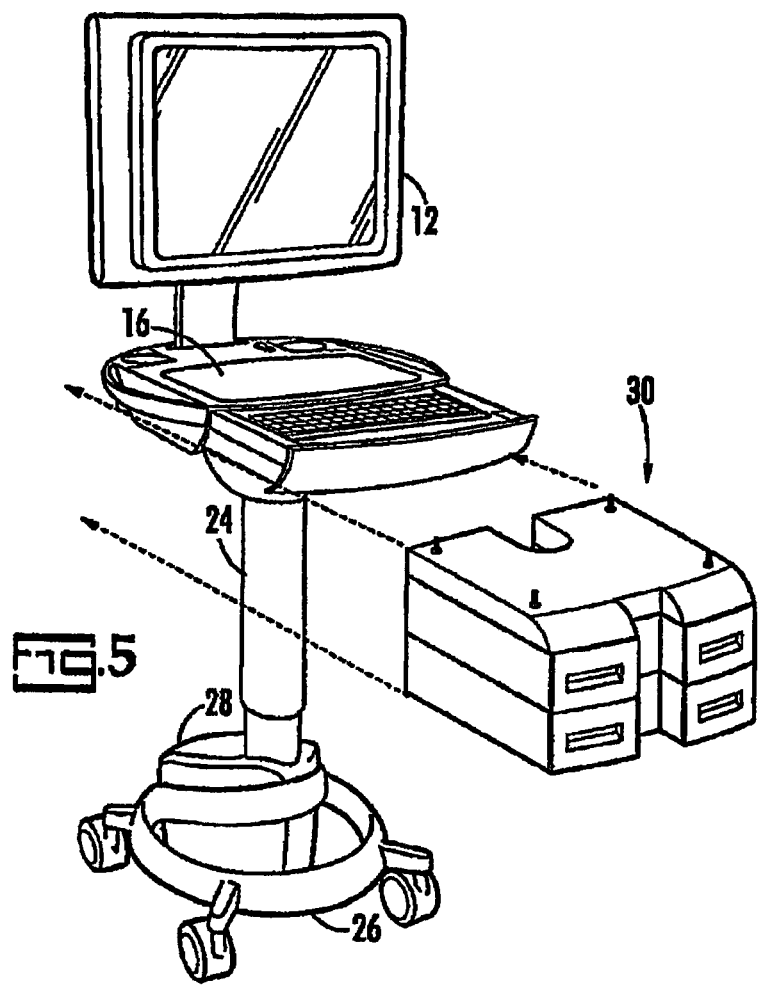

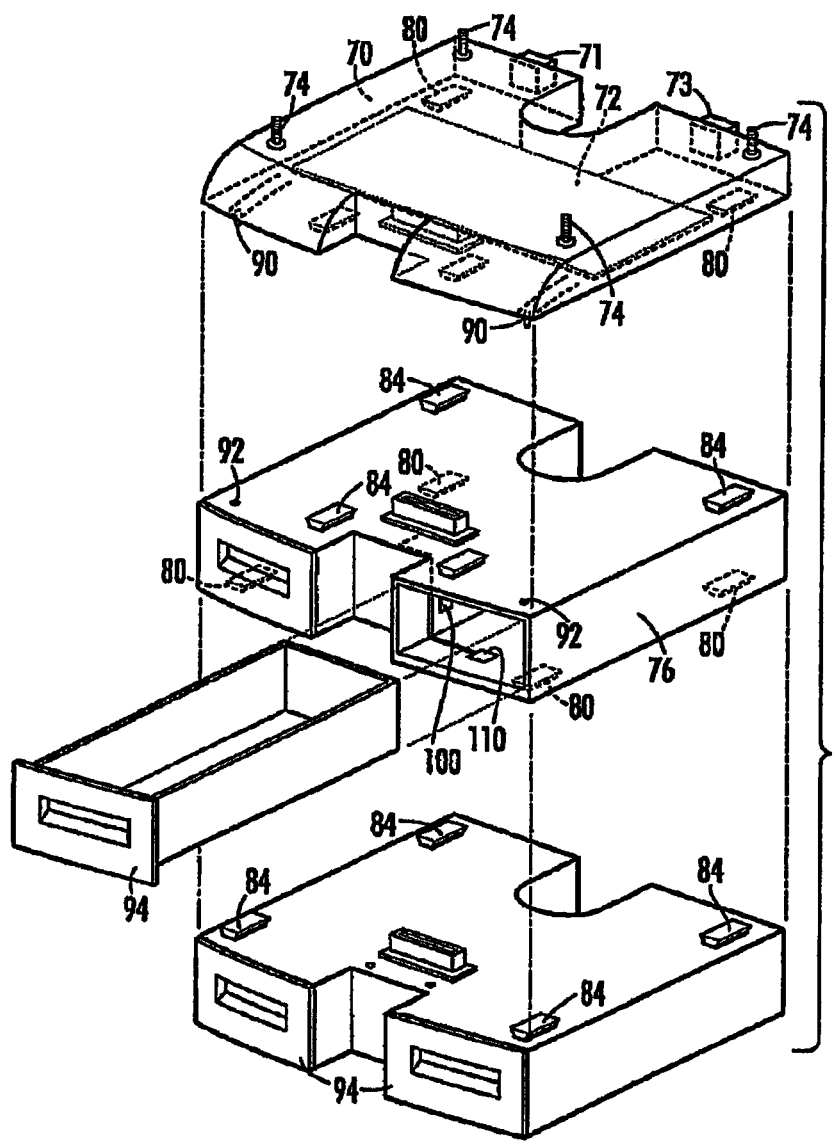

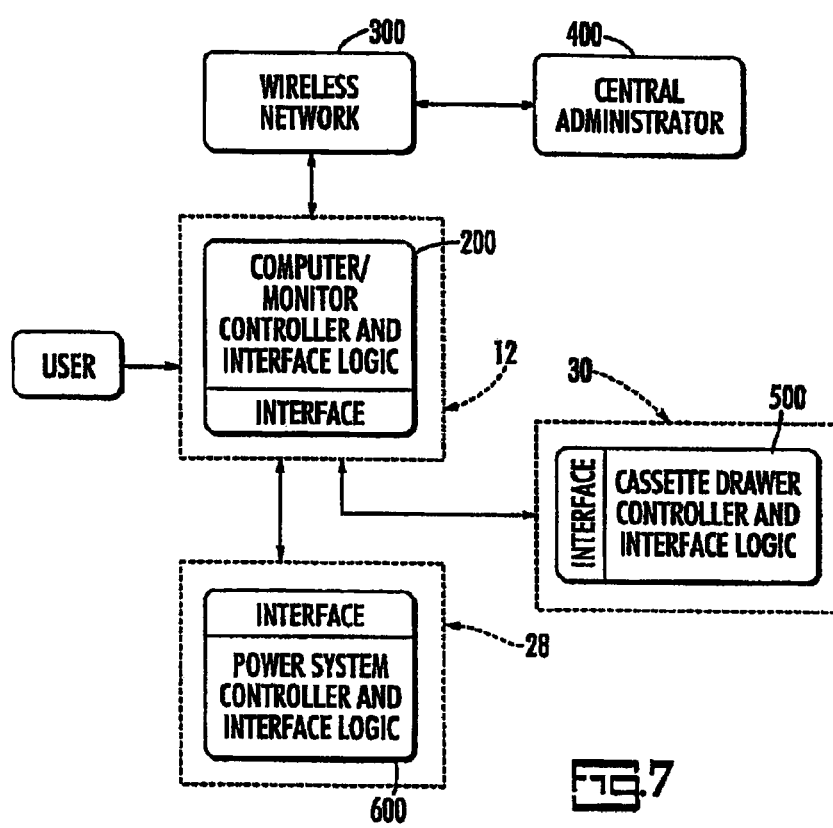

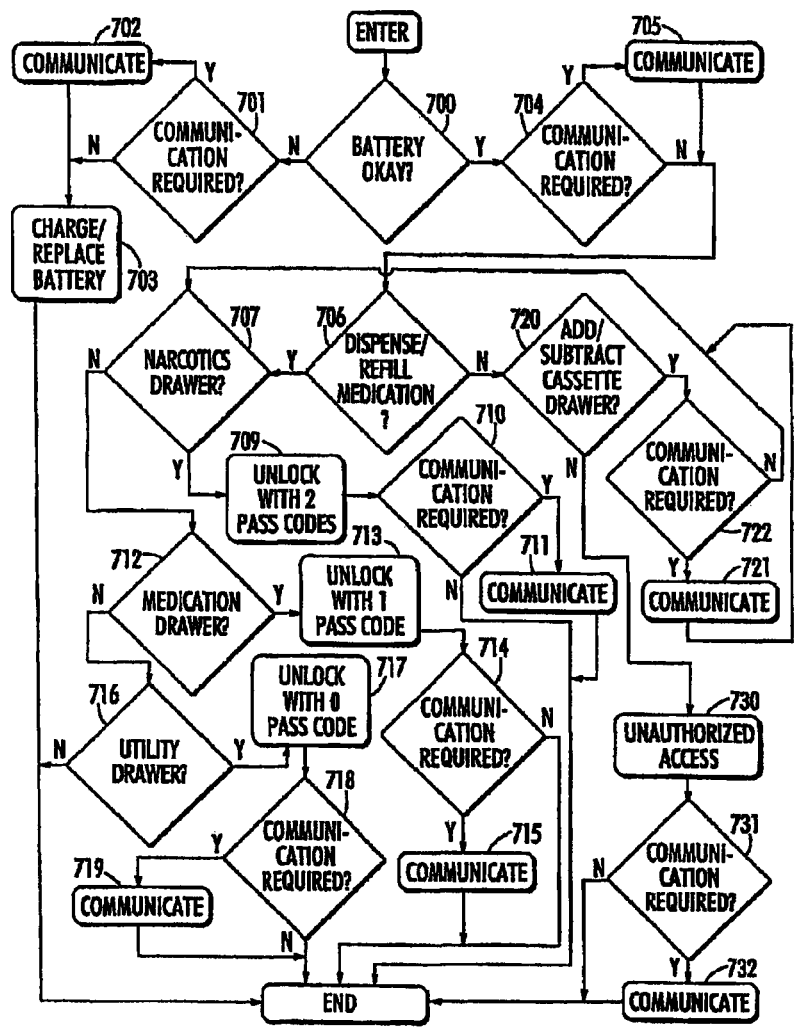

MEDICATION DISPENSING CART

CROSS-REFERENCES TO RELATED APPLICATIONS

This application is a continuation of U.S. patent application Ser. No. 13/461,615, filed May 1, 2012, which is a continuation of U.S. patent application Ser. No. 12/278,263, filed Mar. 11, 2009, which is a 371 of PCT/US2007/03765, filed Feb. 12, 2007, which claims the benefit of U.S. Provisional Application No. 60/772,416, filed Feb. 11, 2006. Each of the foregoing applications is incorporated herein by reference for all purposes.

BACKGROUND OF THE INVENTION

The present invention relates to dispensing medication to patients in hospitals and nursing homes.

In the health care industry, an important component of patient care is medication. Medications, in the form of pills, capsules and liquids, are given to patients to relieve pain, to prevent or eliminate infections, and to treat illnesses and disease. Oftentimes the medications are given in doses that ate repeated at intervals during the day and may be part of a regimen that takes place over several days or even an extended period of time for chronic illness. Medications may have a powerful effect on the body. Some medications should not be taken with other medications or are carefully controlled because of their impact on the patient if too much is administered or because they are subject to abuse by others.

In addition, if the wrong medication is given to a patient, or if the correct medication is given but in too large a dose or too frequently, harm may result. Accordingly, it is important to doctors, nurses and the staff and management of hospitals and nursing homes to make sure their patients take all prescribed medications and only the prescribed medication and to take them in accordance with their prescriptions. Usually, administrative controls and paper records, sometimes augmented by security measures, are used to achieve these objectives.

However, there remains a need for better ways to dispense medications in a controlled manner.

BRIEF SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

According to its major aspects and briefly recited, the present invention is a cart designed for dispensing medication. The cart carries a computer for keeping track of who dispenses what type of medication, when it is dispensed, and that corroborates dispensing information automatically.

The present cart includes a computer with wireless network access and a monitor, a power system having a battery pack to provide power to the computer and monitor, a cassette drawer system having one or more cassette drawers for holding medications, and a security system. Generally, the cassette drawer system, the power system and the security system are software controlled. Access to the cassette drawers is by pass code entry via the computer keyboard or a key override. Each cart user has a different code and only those having valid pass codes or keys can access the drawers. Particular medications, such as narcotics, require a second pass code or second key.

The installation and use of the drawers is sensed by the computer so that it can record who accessed which cassette drawer and when. The use of the computer to track the dispensing of medications enables the cart administrator to compile this information and thereby confirm the medications were given by the cart users as prescribed.

An important feature of the present invention is the use of email from the computer over a wireless network linking all other carts on a system. This feature allows the computer on each cart to keep an administrator informed of the status of each cart, such as the condition of the battery and the use of the cart. It also informs the administrator if there has been an attempt to open a drawer by force.

Another important feature is the cassette drawer system. The drawer system allows additional drawers to be added or drawers to be removed. Drawers that have been added are automatically sensed by the computer and can then be opened only by those who have been given a code that permits access. Once a drawer has been added, it cannot be removed unless it is first opened.

Still another important feature is the use of software to control access. The computer keyboard allows entry of pass codes by users and unlocks only the drawer they wish to access. No separate key pad or lock and key system is needed.

Yet another feature is the use of software to control the raising and lowering of the computer monitor and work station. An electrical switch that is connected to the power system enables a user to adjust the height of the cart work station so that use of the cart can be made both in a standing and seated position.

Still another feature of the present invention is the use of a power system that can be charged independently from the cart. The use of an encapsulated, self-contained power system and battery enables the user to charge the battery in smaller, more confined areas. Furthermore, a user can simply exchange a low charge power system for a fully charged power system without having to remove and replace the internal battery.

These and other features and their advantages will be apparent to those skilled in the art of dispensing medications to patients from a careful reading of the Detailed Description of Preferred Embodiments accompanied by the following drawings.

BRIEF DESCRIPTION OF THE DRAWINGS

FIG. 3 is an exploded perspective view of a base of the medication dispensing cart of FIG. 1.

FIG. 4 is a detailed view of a power system of the dispensing cart of FIG. 1.

FIG. 5 illustrates a cassette drawer system for a dispensing cart.

FIG. 6 is an exploded view of the cassette drawer system of FIG. 5.

FIG. 7 is a block diagram of an operating system for a dispensing cart.

FIG. 8 is a flow chart illustrating the logic for a medication cart system.

DETAILED DESCRIPTION OF THE INVENTION

Figure 1:
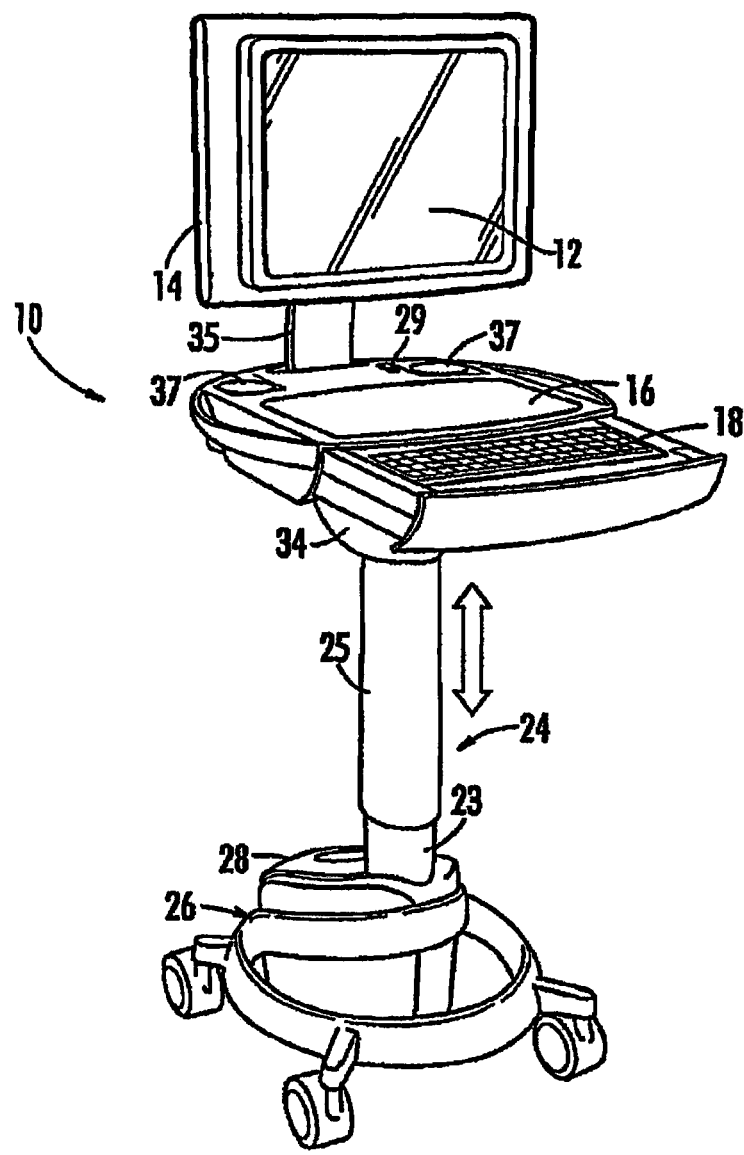
FIG. 1 is a perspective illustration of a medication dispensing cart, according to a preferred embodiment of the present invention.

FIG. 3 is a detailed, exploded, perspective view of the base of a medication dispensing cart, showing the battery in its cover being separated from the battery bracket on indicated in FIG. 1 by reference number 10, includes a computer/monitor 12, preferably with both a computer and a monitor in one unit with the computer behind the monitor and in the same housing 14. Cart 10 also has a work surface 16 with a slide out keyboard 18. There is no security keypad; the keyboard's keypad serves for entry of codes to permit access. Work surface 16 is mounted on top of a mast 24 carried in turn by a rolling base 26. Work surface 16 can optionally include holders for storing items, such as antibacterial lotions and drinks, which the user may need when making rounds with the cart 10.

Figure 2:
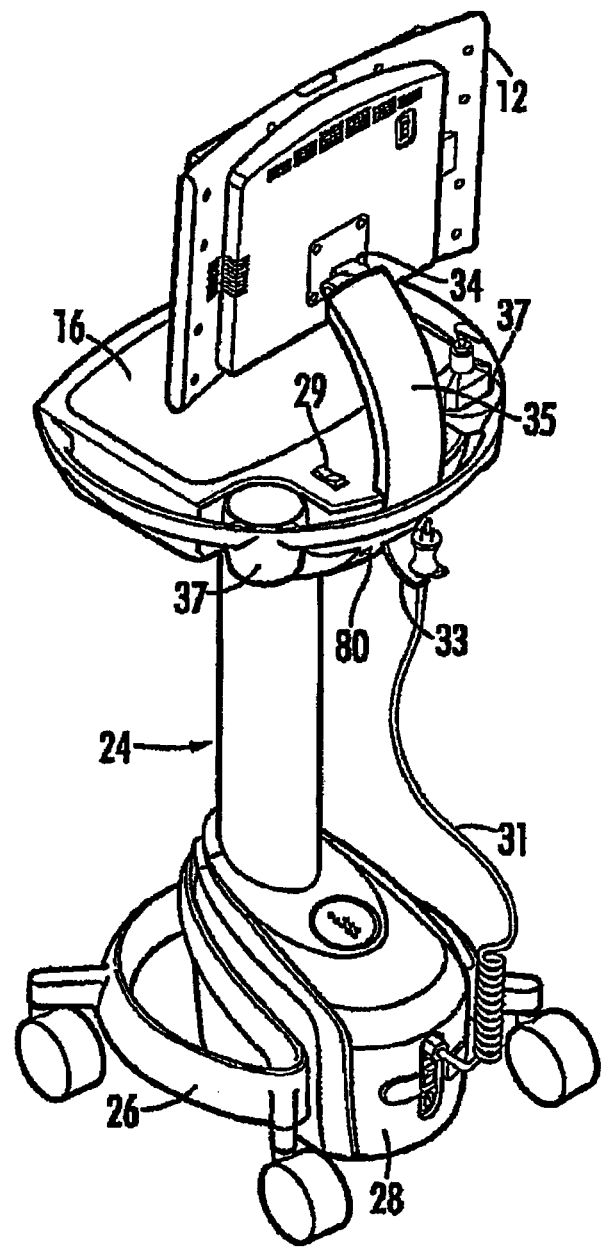
FIG. 2 illustrates a rear, perspective view of a medication dispensing cart according to a preferred embodiment of the present invention.

Referring to FIG. 2, there is illustrated a rear view of the present cart 10 showing computer/monitor 12, work surface 16, mast 24, and a power system 28, which is carried by rolling base 26. Work surface 16 can further include hidden USB port 80 for use if additional electronic devices, such as scanners, need to be employed. Computer/monitor 12 is attached to mast 24 or underneath the work surface through a mount 35 so that the entire top area of the work surface 16 is available to the user. Computer/monitor 12 is mounted using a tiltable bracket 34 so that the angle of viewing computer/monitor 12 can be adjusted to suit the particular user. A clear hard covering is applied over the monitor portion of computer/monitor 12 in order to make computer/monitor less susceptible to scratches and impact. Preferably the covering is about a 1/8.sup.th inch thick and made of acrylic polymeric plastic or other suitable plastic polymer.

Mast 24 is vertically adjustable so that the user can work seated or standing and users of different heights can work comfortably. Preferably, mast 24 is electronically adjustable by pressing a button 29 rather than by turning a hand crank or other mechanical elevating mechanism. As shown in FIG. 1, the mast 24 is telescoped, with an outer mast member 25 dimensioned to receive an inner mast member 23. This arrangement enables the raising and lowering of the computer/monitor 12 and work surface 16. The raising and lowering of the mast 24 can be controlled by an electrical switch 29 that is connected to the power system 28 and mechanical means (not shown), such as a screw/nut drive system that utilizes a number of small balls (ball screw). In operation, a user would press the button 29 in one direction, such as forward, to activate the electrical switch 29 to lower the mast 24, and in another direction, such as backward, to activate the electrical switch 29 to raise the mast 24. The electrical switch 29 provides input to the power system 28, which controls the raising and lowering of the mast 24 through an actuator connected to the mechanical means. Alternatively, the power system can also include a weight sensor connected to the actuator that can be used to override the raising and lowering of mast 24 based on the weight of the work surface 16 and computer/monitor 12. For example, if the combined weight of the work surface 16 and computer/monitor 12 exceeds a preset, desired weight, the actuator will be tripped, and the mast 24 will no longer be moveable through the use of the button 29.

Power system 28 is illustrated in further detail in FIGS. 3-4. As shown, power system 28, which is connected through mast 24 to computer/monitor 12, includes a power system controller (not shown) and a battery 27 that is carried in a battery bracket 50 held in rolling base 26. As discussed, the battery 27 can be charged in combination with the cart 10 or independently of the cart 10, through a power cord 31. Thus, work surface 16 further includes a power cord 31 plug rest 33 (shown in FIG. 2) for conveniently storing the power cord 31 when the cart 10 is being moved or is not in the vicinity of a power source. Battery 27 can be fixed to battery bracket 50 with a variety of mechanical fasteners. In a preferred embodiment, battery 27 is fixed to battery bracket by two screws 52. By removing screws 52, battery 27 and its associated electronics can be removed from bracket 50 to expose the wiring connections. Once the wiring connections are disconnected, battery 27 can be lifted free using its handle 56. Battery 24 is still in a cover 58 and may remain in cover 58 during recharging.

In the event battery 27 needs to be replaced altogether, the screws 60 holding battery 27 in its cover 58 are removed, then the battery hold down screws 62 are removed and finally, battery 27 can be disconnected and replaced. It will be clear that having both a battery cover 58 that stays with battery 27 while battery 27 is either in service or being recharged, and which battery 27 and cover 58 can be quickly removed from cart 10, makes it faster and easier to keep fully charged batteries on carts 10.

As discussed, battery 27 can be charged in combination with the cart 10 or independently of the cart 10, through a power cord 31. Thus, work surface 16 further includes a power cord 31 plug rest 33 for conveniently storing the power cord 31 when the cart 10 is being moved or is not in the vicinity of a power source. Additionally, power system 28 can be equipped with an LED indicator to show when the batter 27 is charging and/or fully charged.

Battery 27 is designed to last through at least one shift of eight hours before requiring recharging, preferably about 10 hours. In addition, each battery is connected to the balance of cart 10 using a "Y" electrical connector 61 that permits a second, fully charged battery 27 to be connected (for "hot swapping") to the unused part of the Y connector, and then the first battery 28 can be removed from the battery bracket and disconnected from the Y connector without loss of power, or data, to computer/monitor 12, and the second battery can then be installed into the battery bracket. The connections that hold battery 28 in its bracket are designed for quick release so battery change out takes but a few minutes at most.

Referring now to FIG. 5, cart 10 preferably includes a cassette drawer system 30. As illustrated, at least one cassette drawer system 30 can be carried below work surface 16. An exploded, detailed view of the cassette drawer system 30 is shown in FIG. 6. Cassette drawer system 30 is preferably modularized, and includes a cassette drawer manager 70, which houses a cassette drawer controller and interface 72 for monitoring the status and activities of cassette drawers and receiving input for computer/monitor 12. The cassette drawer system 30 is generally connected to work surface 16 and wired to computer/monitor 12. More particularly, the top of cassette drawer manager 70 is bolted to work surface 16. Accordingly, cassette drawer manager 70 includes bolt fasteners 74 along its top surface. Optionally, cassette drawer manager 70 includes a first key override lock 71 and a second key override lock 73. In the event drawers need to be opened, and the cassette drawer system 30 or the computer/monitor 12 system is malfunctioning, a first key from authorized users will override the cassette drawer manager controller 72 to open the drawers containing certain medication. If narcotic medication needs to be accessed, a user must insert both a first key and a second key to open the narcotics-containing drawers.

Beneath cassette drawer manager 70, at least one cassette drawer 76 is latched. Depending on the dimensions of the cassette drawer manager 70 and the cassette drawers, up to four drawers 76 can be added. An added drawer 76 cannot be released without opening the drawer. As soon as a drawer 76 is added, it is sensed by controller of computer/monitor 12 and cannot be opened except by a user with an authorizing pass code.

The latching mechanism between the cassette drawer manager 70 and a cassette drawer 76 will be the same as between a first cassette drawer and a second cassette drawer. This latching mechanism is shown in the expanded detailed drawings in FIG. 6. As between the cassette drawer manger 70 and a first cassette drawer, on the underside of cassette drawer manager 70 are a plurality of dovetail-shaped cutout portions 80 that are dimensioned to receive dovetail-shaped projections 84. Similarly, on the underside of each cassette drawer 76 are a plurality of dovetail-shaped cutout portions 80 that are dimensioned to receive dovetail-shaped projections 84 on every lower cassette drawer 78. In operation, dovetail projections 84 simply slide into dovetail cutouts 80.

Once cassette drawer 76 is seated fully into cassette drawer manager manager 70, spring tabs 90 having pins 91, which have been cut out from the bottom surface of cassette drawer manager 70, are cammed upward as drawer 76 is slid into place, and snap downward into corresponding recesses 92 in the top surface of drawer 76. Pins 91 on spring tabs 90 will hold drawer 76 in place until drawer 76 is opened by an authorized person who can then pull tabs 90 down to release drawer 76 from manager 70. Preferably, once cassette drawer manager 70 and any and all additional cassettes are in place, the cassette drawer manager 70 and the cassette drawers are also electronically connected.

As illustrated, cassette drawer manager 70 and cassette drawer 76 are generally U-shaped to facilitate engagement with the mast 24. Each cassette drawer 76 typically has at least two compartments 94 that are independently lockable through electronic locks 100 and that have corresponding sensors 110. Sensors 110 determine if a drawer is open or closed, including of course when a drawer is left open or not fully closed. A drawer that is opened without authorization causes an alarm to sound and initiates an email to the system administrator. All locks 100 are software controlled rather than by using keys. For example, a lock 100 could include a solenoid actuator connected to a lever and controlled by software. Keys can be lost or stolen or fall into the wrong hands. Furthermore, it is easier to change access pass codes using software than to re-key locks. Computer/monitor 12 can be programmed to lock every drawer unless unlocked by a person with the correct level of authorization who enters the correct pass code via keyboard 18. Access to a compartment 94 containing narcotics requires two pass codes; otherwise one pass code unlocks a compartment 94. Each user has his or her own pass code or codes so the user who accesses each drawer is known by the pass code used, as well as the time and date of the access by that user.

Cart 10 is optionally provided with a plug in scanner for reading medication containers and automatically and accurately loading drawers and the computer database with the correct information about the medications being loaded into each drawer. In this way, the system administrator can have a real time inventory of medications in all carts in its system, knowing exactly what type and how much medication is in each drawer of each cart.

Cassette drawer system 30 also has an optional utility cassette 78, which can be used to store such items as rubber gloves, paper cups, tissues, and so forth. Because a utility cassette 78 need not be secured, cassette drawer manager 70 automatically deactivates sensors 110 and locks 100 of utility cassette drawers 78 that become part of the cassette drawer system 30.

A block diagram of the operating system for the cart 10 is shown in FIG. 7. As illustrated, computer/monitor 12 includes a computer controller and interface logic 200 that receives computer controller input and generates computer controller output. For example, computer controller 200 process user input, such as the identity of user, the biometric information of user, pass codes entered by user. Furthermore, computer controller provides output to cassette drawer system 30 relating to the designation of cassette drawers included in the cassette drawer system 30. Significantly, computer/monitor 12 can, in real time, inventory medication as it is loaded and as it used, as well as which user is dispensing the medication. Additionally, computer/monitor 12 is equipped with a wireless network connection, preferably through SMTP (simple mail transfer protocol) so that the user of that cart 10 can communicate with a central administrator 400. Computer/monitor 12 also communicates with administrator 400 without the active assistance of the user. Accordingly, the status and whereabouts of the cart 10 can be constantly and effectively monitored through wireless communication.

As previously described, the cassette drawer system 30 also includes cassette drawer controller and interface logic 500. This cassette drawer controller receives input from the computer controller about the cassette drawers and their designations. Cassette drawer controller, therefore, can lock and unlock drawers based on this input. Furthermore, the cassette drawer controller logs what the drawers do, including when they are opened and by whom. Accordingly, the cassette drawer system 30 has the ability to monitor itself. Similarly, the power system 28 also includes controller and interface logic 600, which monitors the condition of battery 27, and controls the raising and lowering of the mast 24. For example, the condition of the battery 27 when low or when the unit is turning off due to low battery power, power system controller communicates these conditions to computer controller, which in turn reports by email to the administrator. Computer/monitor 12 will also automatically report by email an attempt to break into cart 10, a log of the charging system, a log of the times and the identities of users who have accessed each cassette drawer. Other information can also be reported.

To summarize an embodiment of the logic for the medication cart system, FIG. 8 includes of flow chart. As shown, at 700, a decision is made by medication cart 10 whether the battery 27 is suitable. If the battery 27 is not in a good condition and if communication is required at 701 as to the status of the battery 27, an electronic communication is sent to central administrator at 702. If maintenance is needed, the battery 27 will be charged or replaced at 703. If the battery 27 is in good condition and communication is required at 704, an electronic communication is sent to central administrator at 705.

At 706, a decision is made as to whether medication must be dispensed or refilled. If narcotic medication must be dispensed or refilled at 707, the narcotics drawer is unlocked with two pass codes at 709. If communication as to the status of the narcotics drawer is required at 710, an electronic communication is sent to central administrator at 711. If non-narcotic medication must be dispensing or refilling at 712, the medication drawer is unlocked with on pass code at 713. If communication as to the status of the medication drawer is required at 714, an electronic communication is sent to central administrator at 715. If a utility drawer needs to be accessed at 716, the utility drawer is unlocked with no need for a pass code at 717. If communication as to the status of the utility drawer is required at 718, an electronic communication is sent to central administrator at 719.

If user adds or subtracts a cassette drawer from the cassette drawer system 30 at 720 and communication is required as to the status of the cassette drawer system 30 at 721, an electronic communication is sent to central administrator at 722. If, on the other hand, an unauthorized access to the cassette drawer system 30 is attempted or accomplished at 730, and communication is required as to the status of the cassette drawer system 30 at 731, an electronic communication is sent to central administrator at 732.

It is intended that the scope of the present invention include all modifications that incorporate its principal design features, and that the scope and limitations of the present invention are to be determined by the scope of the appended claims and their equivalents. It also should be understood, therefore, that the inventive concepts herein described are interchangeable and/or they can be used together in still other permutations of the present invention, and that other modifications and substitutions will be apparent to those skilled in the art from the foregoing description of the preferred embodiments without departing from the spirit or scope of the present invention.

What is claimed is:

1. A dispensing cart, comprising:
   a base supported by a plurality of wheels such that the base is suspended above a support surface, wherein the base includes at least one battery;
   a central mast extending vertically up from the base, wherein the central mast is vertically extendible and retractable;
   a work surface operably coupled to the mast such that the work surface is movable up and down by extending or retracting the central mast;
   a monitor having a display screen operably coupled to the work surface so as to be positioned above the work surface;
   a computer that receives power from the battery;
   a drawer system comprising a plurality of drawers positioned between the work surface and the base;
   wherein the cart has a front side in front of the central mast and a rear side rearward of the central mast, wherein the battery is positioned in the base so as to be on the rear side, wherein the display screen is positioned at the rear side, and wherein the drawers are positioned on the front side; and
   a battery bracket to which the battery is removably fixed, wherein the battery comprises a first battery, and further comprising a second battery, wherein the cart is configured such that the second battery is hot swappable with the first battery without loss of power as the first battery is removed from the bracket and the second battery is placed into the bracket,
   wherein both the first battery and the second battery are removably electrically coupled to the computer by a connector such that the second battery is configured to provide power to the computer while the first battery is removed from the bracket.

2. A dispensing cart as in claim 1, further comprising a housing to which the monitor is coupled, and wherein the computer is disposed in the housing behind the monitor.

3. A dispensing cart as in claim 1, wherein the drawer system comprises a drawer housing, and wherein the drawers are vertically stacked and slidable within the drawer housing.

4. A dispensing cart as in claim 3, further comprising a mechanism to couple the drawer housing to the work surface.

5. A dispensing cart as in claim 1, wherein the mast comprises an inner mast member and an outer mast member.

6. A dispensing cart as in claim 1, wherein the battery has a handle.

7. A dispensing cart as in claim 1, further comprising a power cord that extends from the battery to the monitor.

8. A dispensing cart as in claim 1, wherein the base circumscribes the mast.

9. A dispensing cart as in claim 1, wherein the cart includes four wheels, with two of the wheels being at the front side and the other two wheels being at the rear side.

10. A dispensing cart as in claim 1, wherein the support surface has a front and a rear, and further comprising a bracket mounted to the rear of the support surface that extends vertically upward from the support surface, and wherein the monitor is coupled to the bracket.

11. A dispensing cart as in claim 1, further comprising a pull out keyboard disposed beneath the support surface and above the drawer system.

* * * * *